(12) United States Patent
Uzunbajakava et al.

(10) Patent No.: US 8,094,311 B2
(45) Date of Patent: Jan. 10, 2012

(54) SPECTROSCOPIC METHOD OF DETERMINING THE AMOUNT OF AN ANALYTE IN A MIXTURE OF ANALYTES

(75) Inventors: Natallia Uzunbajakava, Eindhoven (NL); Aleksey Kolesnychenko, Eindhoven (NL); Antonius Theodorus Martinus Van Gogh, Eindhoven (NL); Gert 'T Hooft, Eindhoven (NL); Frank Jeroen Pieter Schuurmans, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 823 days.

(21) Appl. No.: 11/912,342

(22) PCT Filed: Apr. 26, 2006

(86) PCT No.: PCT/IB2006/051307
§ 371 (c)(1),
(2), (4) Date: Oct. 24, 2007

(87) PCT Pub. No.: WO2006/114773
PCT Pub. Date: Nov. 2, 2006

(65) Prior Publication Data
US 2009/0268203 A1 Oct. 29, 2009

(30) Foreign Application Priority Data
Apr. 28, 2005 (EP) .................................. 05103480

(51) Int. Cl.
*G01N 21/31* (2006.01)
(52) U.S. Cl. ...... 356/436; 356/326; 702/25; 250/339.12
(58) Field of Classification Search .................. 356/436, 356/300, 310, 328, 445, 326; 250/339.01, 250/339.02; 702/25
See application file for complete search history.

(56) References Cited

U.S. PATENT DOCUMENTS

| | | | |
|---|---|---|---|
| 5,751,418 A | 5/1998 | Kimura | |
| 6,078,389 A | 6/2000 | Zetter | |
| 6,176,323 B1* | 1/2001 | Weirich et al. | 175/40 |
| 6,198,531 B1* | 3/2001 | Myrick et al. | 356/300 |
| 6,529,276 B1 | 3/2003 | Myrick | |
| 6,963,399 B2* | 11/2005 | Cargill et al. | 356/328 |
| 7,115,229 B2* | 10/2006 | Zenhausern | 422/68.1 |
| 7,405,825 B2* | 7/2008 | Schuurmans et al. | 356/326 |
| 7,671,973 B2* | 3/2010 | Van Beek et al. | 356/39 |
| 7,697,141 B2* | 4/2010 | Jones et al. | 356/445 |
| 2002/0171834 A1 | 11/2002 | Rowe | |
| 2004/0021078 A1 | 2/2004 | Hagler | |
| 2004/0218172 A1* | 11/2004 | DeVerse et al. | 356/300 |
| 2008/0094623 A1* | 4/2008 | Schuurmans et al. | 356/306 |
| 2008/0309930 A1* | 12/2008 | Rensen | 356/300 |

* cited by examiner

FOREIGN PATENT DOCUMENTS

| | | |
|---|---|---|
| WO | 2004057284 A1 | 7/2004 |
| WO | 2005062006 A1 | 7/2005 |

*Primary Examiner* — Sang Nguyen

(57) ABSTRACT

The invention relates to a multivariate calibration which can be used when the optical system used for that method does not comprise a multi-channel detector such as a CCD sensor or a line array of photodiodes. An optical system without a multi-channel detector doesn't allow to carry out preprocessing steps. Thus there is the need to carry out these preprocessing steps in another way. It is suggested to partially replace the preprocessing step by a measurement of the optical signal, whereby the measurement comprises transmitting or reflecting the optical signal by an optical element, thereby weighing the optical signal by a spectral weighing function. The advantage of the invention is to teach how such an optical system without a bulky and expensive CCD sensor can be used to carry out a multivariate calibration and preprocessing steps.

13 Claims, 8 Drawing Sheets

SPECTROSCOPIC METHOD OF DETERMINING THE AMOUNT OF AN ANALYTE IN A MIXTURE OF ANALYTES

The present invention relates to spectroscopy analysis methods and spectroscopic devices. More particularly, it refers to improvements in carrying out a multivariate calibration.

Spectroscopic analysis systems can be used for analysing which compounds are comprised at which concentrations in a sample. It is well known that light interacting with the sample carries away information about the compounds and their concentrations. The underlying physical processes are exploited in optical spectroscopic techniques in which light of a light source such as a laser, a lamp or a light emitting diode is directed to the sample for generating an optical signal which carries this information.

For example, light may be absorbed by the sample. Alternatively or in addition, light of a known wavelength may interact with the sample thereby generating light at a different wavelength, for example due to a Raman process. Light can be absorbed and re-emitted at a different wavelength during a fluorescence process. The transmitted and/or generated light then constitutes the optical signal which may also be referred to as the spectrum. The relative intensity of the optical signal as a function of the wavelength is then indicative for the compounds comprised in the sample and their concentrations.

To identify the compounds comprised in the sample and to determine their concentrations the optical signal has to be analysed.

If a particular analyte in a mixture containing several compounds/analytes is to be spectroscopically quantified, its amount can be estimated on the basis of intensity of a single spectral band. This however is only the case when no spectral overlap occurs between different compounds present in a mixture.

More often, however, one faces the task of quantifying the component of interest in a complex mixture where the spectra of individual analytes overlap. In this case a reliable quantitative analysis can no longer be performed in the basis of the intensity of a single spectral band, since other components also contribute to the overall intensity in the same spectral region.

Multivariate calibration is a widely used technique to quantify the amount of a pre-selected analyte (also called the analyte of interest) in complex mixtures. Complex mixtures are characterized by a considerable overlap between the optical spectra of individual analytes. The method takes signal variations in the entire spectrum into account, for example at multiple wavelengths. This makes it advantageous over univariate techniques, which only consider the intensity which corresponds to a single wavelength.

In multivariate calibration a spectral pattern for a particular analyte of interest is identified from the spectra of mixtures with known amounts of the analyte of interest. These mixtures form the so-called training set. The magnitude of the pattern is evaluated mathematically using computational algorithms.

The multivariate calibration procedure can be summarized as follows. First, during the so-called calibration step the optical spectra of the training set are acquired for all wavelengths. The spectra obtained are thus full-length spectra. Using dedicated software a specific pattern, a so-called regression vector, is obtained based on the measured spectra.

A regression vector correlates with the property of interest, e.g., with the amount of the component of interest, but is orthogonal to the spectra of other constituents, referred as interferents.

A regression vector has positive and negative components. Positive components correlate with spectral signature of the analyte of interest and negative components correlate with spectra of the interferents.

During the next step, the so-called prediction step, an optical spectrum of the sample with unknown concentration of the component of interest is acquired. Prediction of the concentration of the analyte of interest is carried out by calculating the inner product (the dot product) of the regression vector and the optical spectrum of the sample with unknown composition.

For a successful implementation of a multivariate calibration it is essential to know the spectral weighing functions, i.e., the regression vectors, corresponding to the compounds of interest. The spectral weighing function may be obtained by performing a principal component analysis of a set comprising N or more spectra (called the training set) of mixtures with known concentration of the analyte of interest, where N is an integer. Each spectrum comprises the intensity of the corresponding optical signal at M different wavelengths where M is an integer as well. Typically, M is much larger than N. Each spectrum containing M intensities at corresponding M wavelengths constitutes an M dimensional vector whose M components are these intensities. These vectors are subjected to a linear-algebraic process known as singular value decomposition (SVD) which is at the heart of principal component analysis and which is well understood in this art.

One skilled in art should understand that the suggested here methods are not restricted to SVD only. There are other computational algorithms that allow calculation of a regression vector such as NIPLS, SIMPLS or PCR.

As a result of the SVD a set of N eigenvectors $z_n$ with n being a positive integer smaller than N+1 is obtained. The eigenvectors $z_n$ are linear combinations of the original N spectra and often referred to as principal component vectors. Typically, the principal component vectors are mutually orthogonal with $|z_n|=1$, i.e., the eigenvectors are orthonormal.

Using the principal component vectors $z_n$, the optical signal of a sample comprising the compounds of unknown concentration may be described by the combination of the normalized principal component vectors multiplied by the appropriate scalar multipliers:

$$x_1 z_1 + x_2 z_2 + x_3 z_3 + x_4 z_4 + \ldots + x_n z_n \quad \text{(equation 1)}$$

The scalar multipliers $x_n$ with n being a positive integer smaller than N+1 may be considered the amplitudes of the principal component vectors $z_n$ in a given optical signal. Each multiplier $x_n$ can be determined by treating the optical signal as a vector in the M dimensional wavelength space and calculating the inner product (the dot product) of this vector with a principal component vector $z_n$. The result yields the amplitude $x_n$ of the optical signal in the direction of the normalized eigenvector $z_n$.

Once the principal component vectors $z_n$ have been found, a regression vector is obtained as a linear combination of k principal component vectors. In most cases k<=N, whereby k=1 and k=N are rather exceptional cases. Further on, a regression vector is derived also considering a vector, which contains the concentrations of the analyte of interest in the training set mixtures. This vector has dimensionality equal to N (where N is the number of samples in the training set).

Depending on the algorithms used, in order to calculate a regression vector, a matrix containing spectra of the training set and a vector containing concentrations are considered either simultaneously or step-wise.

Depending on the algorithms used, either a regression vector is calculated for each of the individual analytes of interest, or a single common regression vector is calculated which allows to predict the concentrations of several different analytes of interest.

U.S. Pat. No. 6,529,276 B1 by Myrick et. al. describes an optical analysis system in which the optical signal is analysed by dedicated hardware comprising an optical filter. This optical filter has a transmission and a reflection which depend on the wavelength, i.e., it is designed to weigh the optical signal by a spectral weighing function which is given by the wavelength dependent transmission. The spectral weighing function is chosen such that the difference between light transmitted through the filter and light reflected from it is directly proportional to the concentration of a particular analyte. Such an optical filter is also referred to as a MOE (multivariate optical element). The transmitted and reflected intensities may be conveniently detected by a detector, for example by a photo diode.

It should be emphasized that in the system proposed by Myrick et al. there is no need to register full-length spectra, i.e., there is no need to use a multi-channel detector during the prediction step, but that a multi-channel detector is still to be used to register full-length optical spectra of the training set, i.e., for the calibration step. This makes the system compact and decreases its cost considerably, making it advantageous over conventional spectrometers, which record full-length spectra also during the prediction step and require an expensive and sometimes bulky multi-channel detector.

The system of Myrick et. al. however has several disadvantages. One drawback is that for each analyte a dedicated optical filter with a characteristic spectral weighing function must be designed, manufactured and used. This increases the operating costs even further and makes the system static and inflexible. Furthermore, if several analytes should be detected a proper filter needs to be placed into the beam path during the prediction step. The system has thus moving parts, the positions of which must be carefully selected. Another disadvantage is that the system of Myrick et. al. needs an optical element with a sharp filter response, such that the optical element requires the deposition of additional layers on its surface. An optical element with multiple layers however decreases the filter efficiency and increases its cost. Still another disadvantage is that the MOE of Myrick et al. is based on an interference filter. In order to weigh the optical spectrum with the weighting factors corresponding to both positive and negative values of a regression vector two measurements and two light detectors, e.g. two photodiodes, are always necessary.

In many cases, the determination of a regression vector requires preprocessing steps to be performed on the optical spectra of the training set prior to mathematical derivation of a regression vector. Very often applications of preprocessing steps improve the accuracy of the analysis. It must be emphasized that identical preprocessing steps should be performed both for the spectra of the training set (during the calibration) and for the spectra of mixtures in which the concentration of the component of interest is to be predicted (during the prediction).

As outlined above, the optical system of Myrick et. al. has the advantage that no multi-channel detector for the prediction step is needed. This however is automatically complemented by the disadvantage that for mathematical reasons pre-processing steps cannot be carried out by computer software any longer. Thus there is a need for a method which teaches how to carry out preprocessing steps in such a case.

It is an object of the invention to show how pre-processing steps can be carried out by a spectroscopic system, in particular a system for carrying out a multivariate calibration, which is adapted to determine the concentration of an analyte in a mixture of analytes.

Another object of the invention is to reduce the workload for determining the concentration of an analyte in a mixture of analytes, and that the above-mentioned spectroscopic system is particularly simple in design.

This object and other objects are solved by the features of the independent claims. Further embodiments of the invention are described by the features of the dependent claims. It should be emphasised that any reference signs in the claims shall not be construed as limiting the scope of the invention.

According to the present invention the above-mentioned object is solved by an optical system and a corresponding spectroscopic method of determining the amount of a preselected analyte in a mixture of analytes with the help of a regression vector associated with said pre-selected analyte (also called the analyte of interest). The determination comprises at least one pre-processing step. Preferably the spectroscopic method is a multivariate calibration. The method is a method in which no signal is detected which directly yields a regression vector. Instead, at least one pre-processing step is carried out in order to extract the magnitude of a regression vector for the analyte of interest, such that the concentration of the analyte of interest in a mixture of analytes can be determined. Preferably, the mixture is a complex mixture in which the spectra of individual analytes overlap. The method comprises calculations for carrying out the at least one pre-processing step, whereby the calculations are at least partially substituted by a measurement of the optical signal. Thus a calculation step, which would have otherwise has to be carried out on a computer by a suitable computer program product, together with a prior detection of a full-length spectrum on a multi-channel detector, is replaced by measurement step. In this replacement or substitution a measurement value replaces/substitutes the value of a mathematical term. The measurement comprises transmitting or reflecting the optical signal by an optical element, thereby weighing the optical signal by a spectral weighing function.

The advantage of this approach is that pre-processing steps, which in the past have been performed by means of registering the full-length spectrum (many wavelength) using a multi-channel detector and which are impossible to carry out when no such a detector is used, are now possible without such a multi-channel detector.

Pre-processing steps pre-process optical signals/spectra and serve to improve the accuracy of the method. Identical pre-processing steps should be done on the optical signals of the training set used to derive a regression vector and on those from the real measurements in the prediction step.

A multitude of pre-processing steps are conceivable in the context of this invention. As explained above, the pre-processing steps are carried out in the framework of a multivariate calibration. This method allows the prediction of analyte concentration, i.e. the amount of the analyte, by calculating an inner product between the regression vector $R(\lambda)$, $\lambda$ being a wavelength, and the optical spectrum, $S(\lambda)$ obtained from the sample. The predicted concentration [c] of the analyte is then $$[c] = RS^T = \sum_{i=1}^{M} R(\lambda_i) S(\lambda_i) \quad \text{(equation 2)}$$

with $S^T(\lambda)$ being the transpose of the optical spectrum. The numbers i and M are integers which serve to sum over the wavelength dimension as in the formulae which follow.

Pre-processing steps concern mathematical operations with equation 2 and can be:

1) A Differentiation of an Optical Spectrum

A differentiation of equation 2 is expressed by $$[c] = R(\lambda) \frac{dS(\lambda)^T}{d\lambda} = \sum_{i=1}^{M} R(\lambda_i) \frac{dS(\lambda)}{d\lambda}\bigg|_{\lambda_i}, \quad \text{(equation 3)}$$

Whereby $d\lambda=1$ is assumed. This pre-processing step removes a slowly varying background signal or a constant baseline. This may for example be due to an instrumental drift. Typically, a slowly varying contribution is not correlated to the concentration of the compound of interest and has thus to be eliminated to get a more accurate result.

2) A Mean Centering

Considering mean centering, equation 2 is written as $$[c] = RS^T = \sum_{i=1}^{M} R(\lambda_i)(S(\lambda_i) - \overline{S(\lambda_i)}) \quad \text{(equation 4)}$$

whereby $$\overline{S(\lambda_i)} = \frac{1}{N} \sum_{j=1}^{N} S_j(\lambda_j) \quad \text{(equation 5)}$$

The numbers j and N are integers which serve to sum over all optical signals of the training set as in the formulae which follow. Equation 5 denotes the mean value of the optical signals/spectra of the training set, and $S_j$ are the optical signals/spectra of the training set.

Mean centering serves to subtract features common to all optical signals of the training set, whereby the training set is used for determining the regression vector. This decreases the number of principal components necessary to explain a variation present in the measured optical signals.

3) A Scaling of the Variable for Unit Variance

This pre-processing steps gives all spectral components an equal weight. Variations of the spectral components are thus equally high. Without these steps the likelihood that the above-mentioned model fails will increase.

Equation 2 is written as $$[c] = RS^T = \sum_{i=1}^{M} R(\lambda_i)\left(\frac{S(\lambda_i) - \overline{S(\lambda_i)}}{\sigma(\lambda_i)}\right) \quad \text{(equation 6)}$$

with $$\sigma(\lambda_i) = \frac{1}{N}\sqrt{\sum_{j=1}^{N}(S_j(\lambda_i) - \overline{S(\lambda_j)})^2} \quad \text{(equation 7)}$$

being the standard deviation of the spectral component $S(\lambda_i)$ for each wavelength $\lambda_i$.

4) An Averaging Operation

Averaging the signal over the neighbouring wavelength is performed as follows:

$$[c] = \left(\sum_{i=1}^{M} R(\lambda_i) \frac{S(\lambda_{i+1}) + S(\lambda_i)}{\text{const}}\right) = \quad \text{(equation 9)}$$

$$\frac{1}{\text{const}}\left(\sum_{i=1}^{M} R(\lambda)s(\lambda_{i+1}) + \sum_{i=1}^{M} R(\lambda_i)S(\lambda_i)\right)$$

Whereby [c] denotes the predicted concentration and const is equal to the number of wavelengths taken for averaging. The averaging operation helps to avoid extra measurements in the case of a significant noise, for example due to background signal, such that the measurement time is reduced.

It should be mentioned that the above-mentioned pre-processing steps are exemplary in nature, such that other pre-processing steps are conceivable for which the present invention can be used.

The above-mentioned method makes use of an optical element which weighs the optical signal by a spectral weighing function. For that purpose a variable multivariate optical element (VMOE) is used. The VMOE might operate in transmissive mode or in reflective mode.

The VMOE might be a spatial light modulator (SLM), for example a liquid crystal display (LCD), a digital mirror device (DMD), a grating light valve, a liquid crystal on silicon (LCOS) or the like. A preferred reflective SLM is the DMD, as a DMD can operate at a high speed, has a high precision, and an efficiency of more than 68%. Moreover, an advantage of DMD's is that they can also be used for the whole optical spectrum, e.g., for ultraviolet light and in the infrared. SLM's are widely available at high volumes at a low price.

The VMOE is used in the following way: the source of the signal illuminates a dispersive element which separates the different wavelengths of the multi-wavelength signal. The dispersive element might be a diffraction grating or a prism or the like. The separated wavelengths then impinge on the VMOE, and are transmitted or reflected by the VMOE. Then the reflected or transmitted signal is focused by focusing means, e.g. a lens, on a detector, e.g. a photo diode. The VMOE thus avoids the use of a multi-channel sensor, for example a CCD sensor or a line array of photodiodes. This makes the whole optical system smaller and less expensive. Furthermore the design of a portable optical system is in some cases impeded by a multi-channel detector, such that the VMOE increases the flexibility in designing the optical system.

The VMOE has a number of advantages. A major advantage of the VMOE is its flexibility. The VMOE can be adjusted to perform the above-mentioned weighing in different ways and for unlimited analytes of interest. It is possible to "display" arbitrary weighing functions with a single VMOE and to change the function in time rapidly. It is thus possible to use the VMOE to weigh the optical signal with a first weighing function, to adjust the VMOE, and then to weigh the optical signal with a second weighing function. This dynamic flexibility can be used to perform pre-processing steps in a flexible way as it will be apparent from the description which follows.

Another advantage of the VMOE is its fast dynamic response and its sharp filter response. The latter advantage refers to its ability to "display" a pattern with narrow spectrum-like bands.

Additional advantages of the VMOE are its low cost, the fact that it is available of-the-shelf, and that it can be used for a broad range of wavelengths throughout all optical spectrum.

Still another advantage is that the VMOE is able to "display" the whole regression vector (i.e. both the positive and the negative components) at once. This helps to reduce the workload for determining the concentration of an analyte in a mixture of analytes, and for simplifying the design of the above-mentioned spectroscopic system. As far as these two advantages are concerned it has to be borne in mind that a regression vector usually has both positive and negative values. When a MOE is used instead, for example the MOE of Myrick et al. based on an interference filter, two measurements with two light detectors are necessary in order to weigh the optical spectrum with the weighing factors corresponding to both positive and negative values of the regression vector.

With the present invention using a VMOE two ways can be chosen to avoid negative values:

A first possibility is to sequentially apply positive and absolute values of the negative components of a regression vector to the VMOE, to detect spectral responses, and then to subtract the spectral responses from the components. This requires only a single photodiode but two sequential measurements.

A second possibility is to add a constant to a regression vector, so that all its values become positive. In other words a biased signal is sent to the VMOE. This requires one photodiode and one measurement step only. The advantage of the second possibility in comparison to the first possibility is that only one measurement is necessary, and that in the case that the VMOE is a LCD is used as a basis for the VMOE, light leakage in the dark state is not an issue.

As already mentioned in the introductory part of the description the VMOE-based optical system, just like the system proposed by Myrick et al., uses no multi-channel detector, e.g. a CCD detector, at least during the prediction step. This means that the above-mentioned pre-processing steps 1 to 4 cannot be carried out by computer software any longer for mathematical reasons.

According to the invention the calculations for carrying out the pre-processing step are partially substituted by a measurement of the optical signal. As far as the above-mentioned examples are concerned the substitution is carried out as follows:

a) Differentiation of an Optical Spectrum

Using finite differences on can write $$\frac{dS(\lambda)}{d\lambda}\bigg|_{\lambda_i} = \frac{S(\lambda_{i+1}) - S(\lambda_i)}{\Delta\lambda} \quad \text{(equation 10)}$$

Inserting equation 10 in equation 3, one obtains $$[c] = \sum_{i=1}^{M} R(\lambda_i)S(\lambda_{i+1}) - \sum_{i=1}^{M} R(\lambda_i)S(\lambda_i) \quad \text{(equation 11)}$$

Whereby $d\lambda=1$ is assumed.

The first term and the second term of this difference can be measured individually in two ways.

A first possibility is as follows: a first measurement is carried out which comprises transmitting/reflecting the optical signal by a SLM. The SLM has a transmittance/reflectance such that it weighs the optical signal $S(\lambda)$ according to the regression vector $R(\lambda)$, i.e. the components of the regression vector constitutes the spectral weighing function. In other words the LCD "displays" the regression vector vector $R(\lambda)$. The optical signal is transmitted/reflected by the SLM, and the transmitted/reflected signal is focused on a single channel detector, e.g. a photodiode. This yields the second term of equation 11.

After the first measurement, the dispersive element is turned which shifts the spectrum with respect to the regression vector. The dispersive element can be a diffraction grating or a prism. Turning the dispersive element can be done by appropriate turning means, for example by a simple motor turning the dispersive element around a predefined axis by a fixed angle. The motor can be electronically controlled.

Then a second measurement is performed with the SLM while using the turned dispersive element. This yields the first term of equation 11. Calculating the difference is a calculation step performed by electronic means, for example a computer. Thus the two terms of equation 11 are each replaced by measurement values.

A second possibility for measuring the two terms of equation 11 is as follows: a first measurement is carried out which consists of transmitting or reflecting the optical signal by a SLM. This is done in the same way as above and yields the second term of equation 11. After the first measurement the SLM is modified, whereby the modification consists in an adjustment of the SLM to weigh the optical signal by a spectral weighing function with a lateral offset, i.e., along the spectral dimension of at least one pixel in comparison to the first measurement. Then a second measurement is carried out with the modified SLM. This yields the first term of equation 11. Calculating the difference is a calculation step performed by the electronic means. Since it is just subtraction of two values, one does not need the full computational power of a personal computer. Thus the two terms of equation 11 are each replaced by measurement values.

The second possibility represents the preferred choice, since there are no moving parts (as the moved grating in the first approach) present in the spectrometer. Furthermore, the time needed for the measurements when applying the second possibility is in some cases shorter than when applying the first possibility.

The adjustment of the SLM between the two measurements serves to modify the pattern "displayed" on the SLM. This pattern is generally controlled by an electric signal sent to the SLM by a signal generator, whereby the signal is proportional to the magnitude of the regression vector. Modification of the above-mentioned pattern is thus achieved by modifying this signal by electronic means, and sending the modified signal to the SLM. At least two modifications are conceivable.

A first possibility is to send a biased signal to the SLM. In this case a constant is added to the regression vector, such that all its components become positive. In this case only a single measurement of the optical signal is necessary with a single photodiode.

A second possibility is to sequentially apply positive values and absolute values of the negative components of a regression vector, to detect the corresponding spectral responses, and to subtract them. This requires two measurements and a single photodiode.

b) Mean Centering

Equation 4 can be written as $$[c] = \sum_{i=1}^{M} R(\lambda_i)S(\lambda_i) - \sum_{i=1}^{M} R(\lambda_i)\overline{S(\lambda_i)} \qquad \text{(equation 12)}$$

The second term is calculated (do note that $\overline{S(\lambda_i)}$ was already estimated prior calculation of a regression vector and regression vector was calculated afterwards), whereby the definition of the mean value of the optical signal given in equation 5 is used. The first term of equation 12 can be substituted by a measurement value derived from measurement in which the SLM "displays" the regression vector vector $R(\lambda)$, in which the optical signal is transmitted/reflected by the SLM, and whereby the transmitted/reflected signal is detected, e.g. by a photo diode.

c) A Scaling of the Variable for Unit Variance

Equation 6 can be written as $$[c] = \sum_{i=1}^{M} R'(\lambda_i)S(\lambda_i) - \sum_{i=1}^{M} R'(\lambda_i)\overline{S(\lambda_i)} \qquad \text{(equation 13)}$$

whereby the definition $$R'(\lambda_i) = \frac{R(\lambda_i)}{\sigma(\lambda_i)} \qquad \text{(equation 14)}$$

has been used. Calculating equation 14 and the second term of equation 13 is carried out by computer software since the values of the variance and of the mean value were already calculated during the calibration step using the full-length spectra. The first term of equation is substituted by a measurement value in the same way as in case a) above, whereby the SLM is arranged to "display" $R'(\lambda_i)$. Subtracting the two terms is equivalent to multiplying a regression vector vector by a scaled to unit variance optical signal. One should remember that the values of $\sigma(\lambda_i)$ and $\overline{\sigma(\lambda_i)}$ have been already calculated in computer software during the calibration step, since identical pre-processing steps are to be applied both during the calibration step and during the prediction step.

d) Averaging Operation

The two terms in equation 9 can each be substituted by a measurement value in the same fashion as in cases a) to c).

In another aspect the present invention relates to a spectroscopic device for quantitative chemical analysis comprising a variable multivariate optical element for performing multivariate calibration in the optical domain. Such a spectroscopic device can be implemented using any embodiment of the spectroscopic method, optical analysis system and/or computer program product of the invention.

Embodiments of the spectroscopic device are particularly advantageous as usage of the variable multivariate optical element (VMOE) for performing the multivariate calibration in the optical domain enables to keep the cost for the spectroscopic device low and enables a compact design. The spectroscopic device uses multivariate calibration (MC) to quantify concentrations of analytes of interest in mixtures with complex composition, such as in food, water, or beverages.

Due to the usage of a VMOE an expensive multi-channel light detector for registration of optical spectra is not necessary for the multivariate calibration. Unlike classical multivariate calibration, VMOE performs at least some of the necessary computations in the optical domain which can make the multi-channel detector redundant.

This way the cost of the spectroscopic device can be dramatically decreased in comparison with prior art spectroscopic devices using multivariate calibration.

In accordance with an embodiment of the invention the spectroscopic device is operable to evaluate a result of the quantitative chemical analysis, such as for providing quality information regarding a sample that has been analyzed. In one application the spectroscopic device analyzes the components of food, such as the percentages of fats contained in the food or the proportions of other ingredients, such as protein, carbohydrates, salts, etc. The results of this quantitative chemical analysis can be evaluated regarding various dietary criteria in order to provide quality information. For example, the quality information is indicative of how healthy a food is in general terms or applying criteria that are specific for a given patient.

In another application the spectroscopic device is used for testing if a food or beverage is consumable without undergoing a substantial health risk. The spectroscopic device is adapted to detect food decay products for testing the food quality. Likewise, the spectroscopic device can be used for beverages quality monitoring and water purity monitoring. Such applications of the spectroscopic device are particularly advantageous for developing countries where the quality of food and/or water is often very low and where reliable food certificates are often not available.

Embodiments of the present invention are particularly advantageous for beverages quality monitoring, especially regarding methanol content of beverage products. Low quality beverage products often contain an increased amount of methanol which has a high lethality risk upon consumption of the beverage product. Embodiments of the spectroscopic device can be used as a mobile and/or portable food and beverage control device for governmental organizations, small businesses and individual consumers.

In accordance with an embodiment of the invention the spectroscopic device has an electronic processing component that is coupled to a storage component. The storage component serves for storage of at least one threshold value and/or at least one condition or rule for use by the electronic processing component in order to evaluate the result of the quantitative chemical analysis. As a result of the evaluation the electronic processing component can provide quality information regarding one or more quality criteria of the sample that has been analyzed.

The result of the quantitative chemical analysis and/or the result of the evaluation, in particular the quality information, can be outputted via a user interface. The user interface can comprise a display for displaying the respective information and/or a printer for printing the respective information. Furthermore, the user interface can comprise one or more control lamps for outputting the quality information.

For example, the user interface can comprise a red control lamp and a green control lamp. The red control lamp is switched on when consumption of the food or beverage is unsafe in accordance with the result of the evaluation whereas the green control lamp is switched on if consumption is safe. In addition there can be a yellow control lamp that would indicate that the quality is questionable or if no precise quality information can be given.

In accordance with an embodiment of the invention the spectroscopic device has a computer interface, such as for interfacing with a computer bus. In particular the spectroscopic device can have a USB interface for coupling the spectroscopic device to a computer, such as a portable or laptop computer. In this instance the computer program for performing the evaluation of the result and/or for performing the necessary spectroscopic computations can be implemented on the external computer system. Likewise the user interface can also be provided by the external computer system.

As can be derived from the description given above the above-mentioned calculations are performed by means of a computer program. In order to carry out the present invention such a computer program has to be modified in that it accepts at least one measurement value in lieu of a value of a mathematical term, said mathematical term being usable for carrying out a pre-processing step.

These and other aspects of the invention will be apparent from and elucidated with reference to the embodiments described thereafter. It should be emphasized that the use of reference signs shall not be construed as limiting the scope of the invention.

Figure 9:
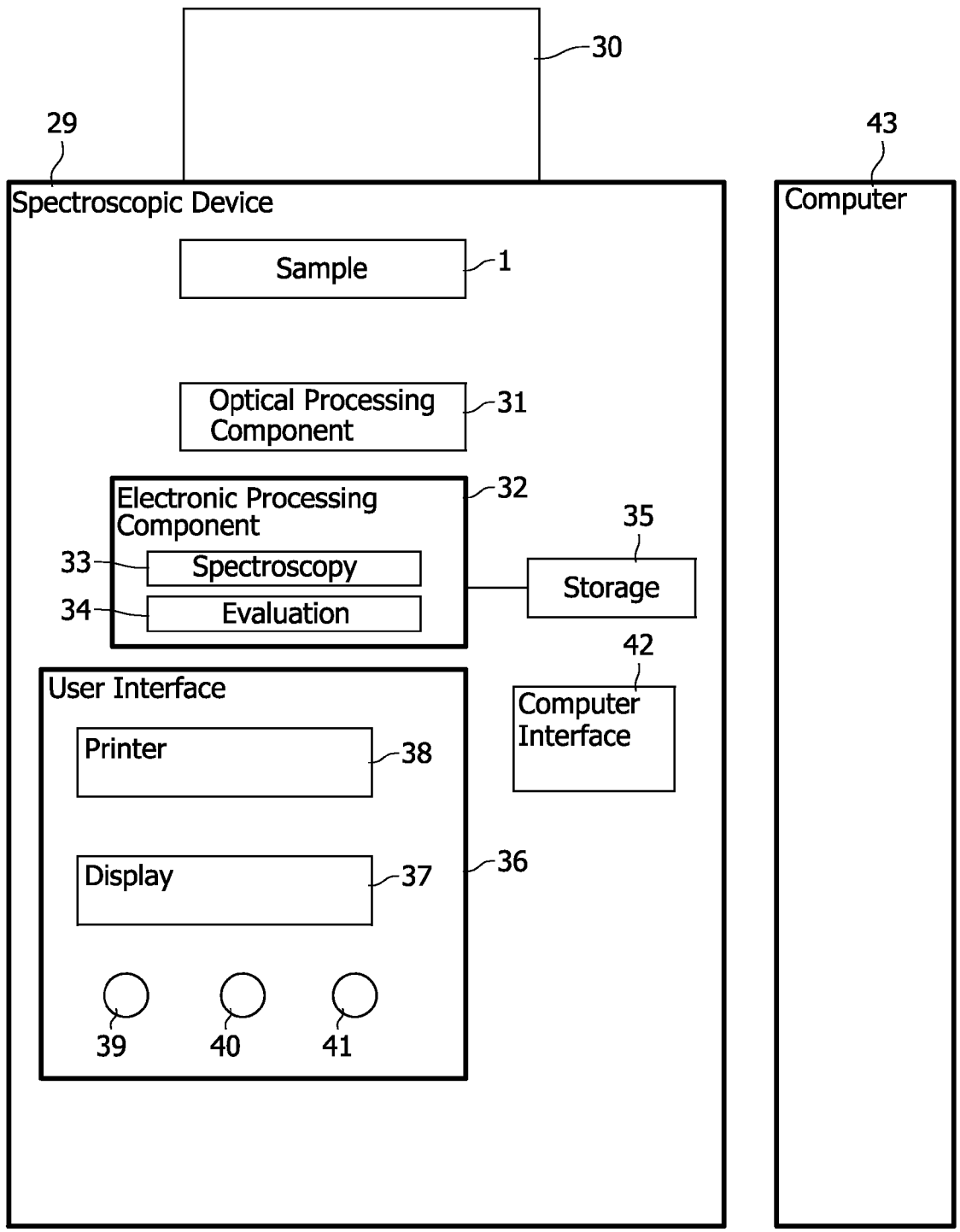
Figure 10:
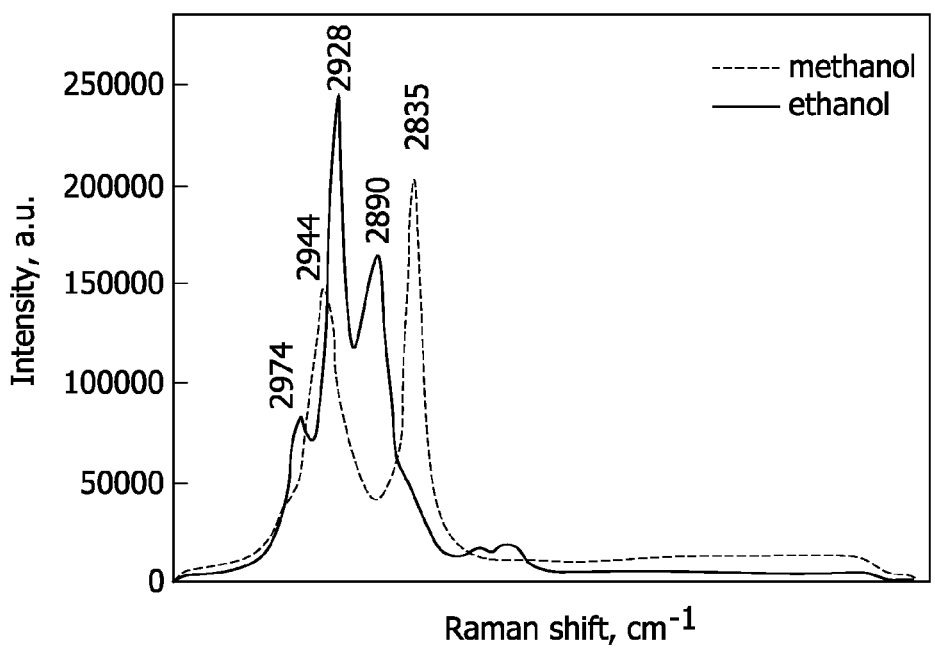
Figure 11:
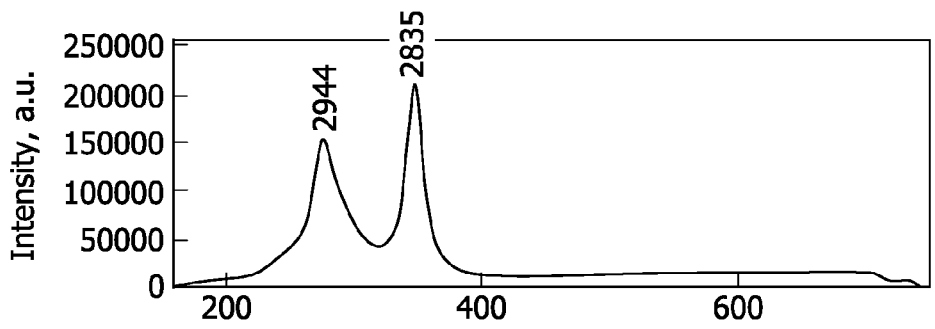
Figure 12:
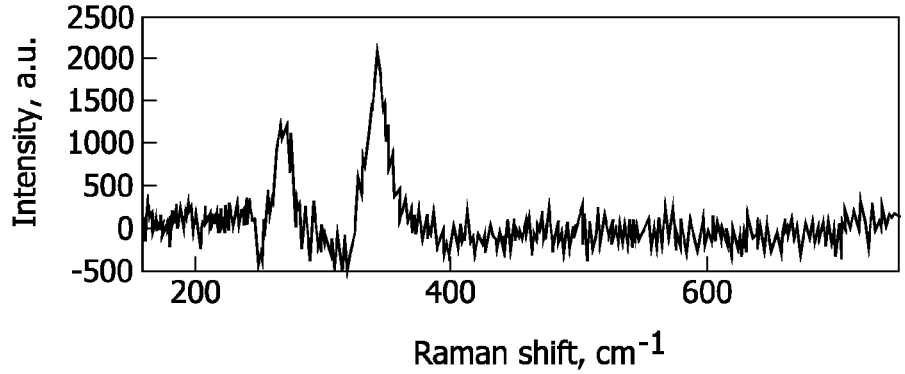

FIG. 9 shows a block diagram of an embodiment of a spectroscopic device of the invention, FIG. 10 shows Raman spectra of 96% ethanol and 99.8% methanol, FIG. 11 shows the Raman spectrum of pure 99.8% methanol, FIG. 12 shows a Raman difference spectrum of a mixture containing 47.2% ethanol and 1.6% methanol in water and 48% ethanol in water, respectively.

Table 1 shows the mass ratios of the components of the training set.

Figure 1:
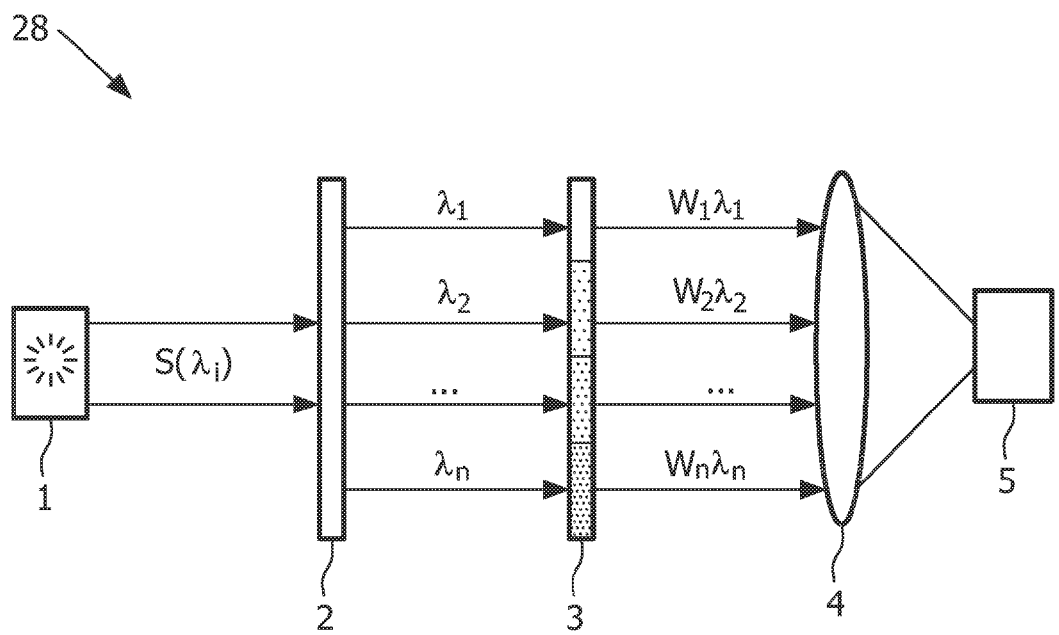
FIG. 1 is a schematic representation of the VMOE concept.

FIG. 1 shows the VMOE concept applied for determining the concentration of an analyte (the analyte of interest) in a complex mixture of analytes. The signal $S(\lambda)$ from sample 1 falls on a dispersive element 2 where the wavelengths $\lambda_i$ are spatially separated. The dispersed signal then impinges on the VMOE, for example a SLM 3. By addressing individual pixels of the SLM 3 their optical transmittance/reflectance is changed in such a way that the individual wavelengths are transmitted/reflected with different weighing coefficients $w_i$. The resulting signal is focused on a single photo diode 5 by means of a lens 4.

If the weighing coefficients $w_i$ are components of a regression vector $R(\lambda$ the transmission/reflection of the signal by the SLM 3 is equivalent to a multiplication of the regression vector by the signal: $R(\lambda_i)S(\lambda_i)$.

Focusing the transmitted signal by a lens 4 is equivalent to a summation over all wavelengths. Thus the setup of FIG. 1 is equivalent to the calculation of the inner product $RS^T$.

By performing the computation of the inner product $RS^T$ in the optical domain using the VMOE device 28 of FIG. 1, an expensive multi-channel light detector that is used in prior art spectroscopic devices is made redundant, thus reducing dramatically the cost.

Figure 2:
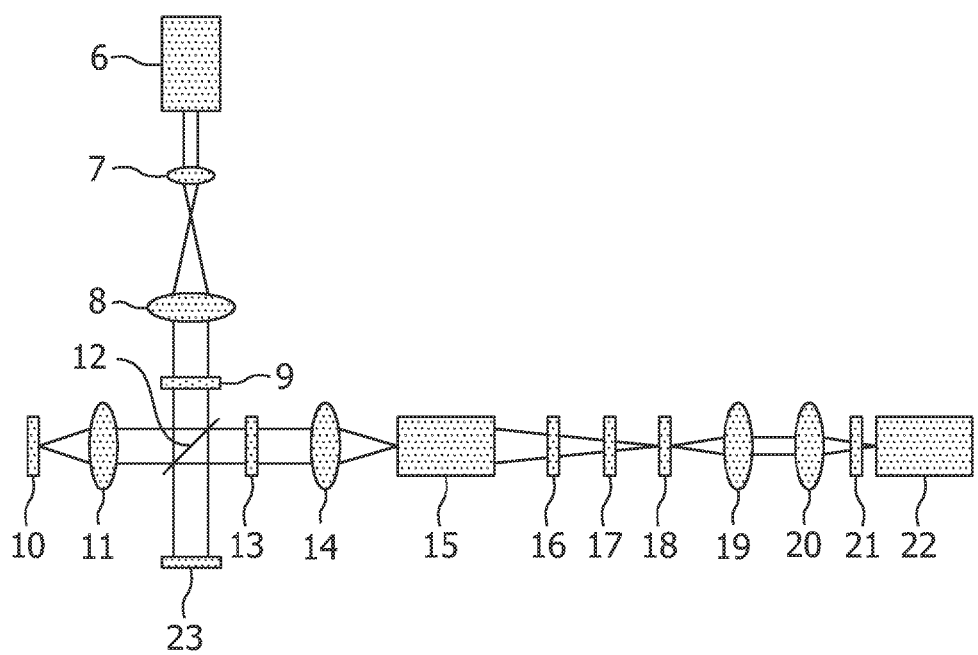
FIG. 2 is the optical system used for measurements during the calibration step for obtaining the regression vectors.

FIG. 2 shows the optical analysis system used for carrying out the method. Light from a laser 6 propagates towards an lens 7, and from there via an achromatic doublet 8 and a half-lambda-wave plate 9 to a dichroic beam splitter 12. The laser 6 is a continuous wave diode-pumped solid state laser emitting a wavelength of 532 nm. The incident light is reflected to the left and is focused by objective 11 on the absorption cell 10. Absorption cell 10 contains a mixture of cyclohexane, acetonitrile and toluene as will be explained below in more detail.

Light emitted from the sample 10 propagates from to the right via objective 11, dichroic beam splitter 12, holographic notch filter 13, achromatic doublet 14, spectrograph 15, retardation film 16, polarizer 17, LC panel 18, two wide-angle lenses 19 and 20, analyser 21, an optical multi-channel analyser (OMA) 22.

The spectrograph 15 contained a grating 2 positioned on a rotary table 25 driven by a motor 24. The motor 24 is arranged to rotate the grating 3 by fixed angles around the axis A, cf. FIG. 3. A power meter 23 was used to control the optical power of the laser 6 during the experiments.

Figure 4:
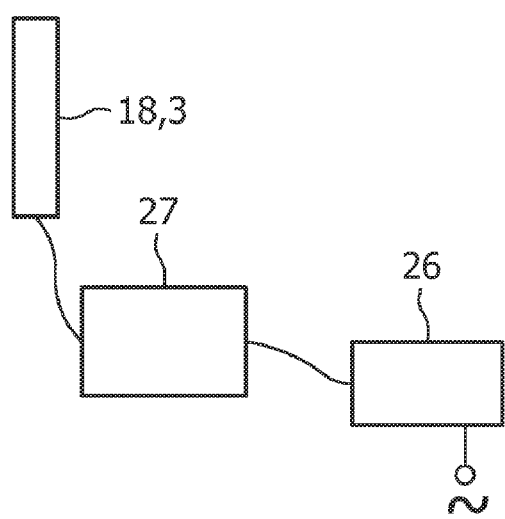
FIG. 4 shows a spatial light modulator receiving modified electric signal to adjust the spectral weighing function which it "displays".

LC panel 18, or generally any SLM 3 receives electric signals to "display" the spectral weighing function. The signals originate from a signal generator 26 and are modified by electronic modification means 27 as described above, cf. FIG. 4.

A prerequisite for carrying out a multivariate calibration is the acquisition of optical signals/spectra of mixtures with known composition, referred to as a training set. As a first step 15 three-component mixtures were chosen with the constraint of constant total mass of each sample. The components were cyclohexane, acetonitrile and toluene. The complete list of the selected mass ratios is given in table 1.

Figure 3:
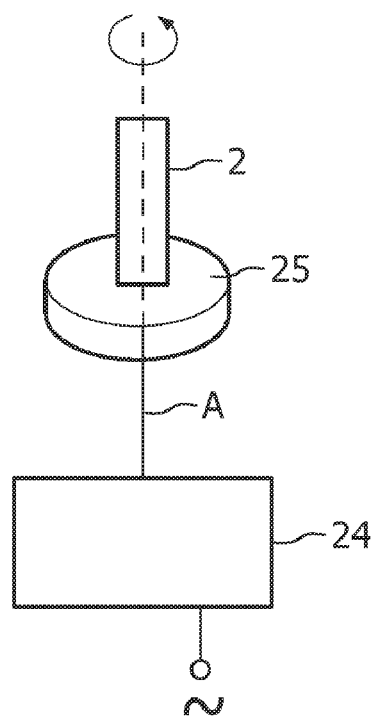
FIG. 3 shows a dispersive element turned by a motor on a rotary table.

In a second step full-length Raman spectra of these 15 mixtures were acquired with subsequent background subtraction. Full-length spectra contain all the wavelengths and are recorded by means of a multi-channel detector. This is necessary for the calibration step in order to calculate a regression vector. FIG. 3 shows the Raman spectra of pure toluene (upper part), acetonitrile and cyclohexane (lower part).

Figure 5A:
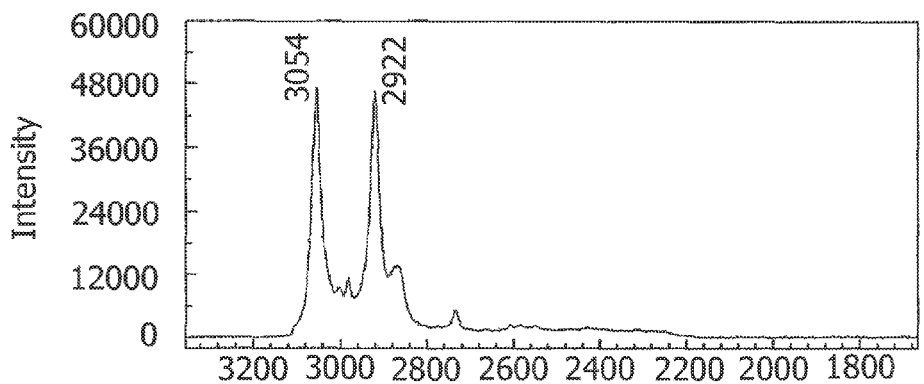
FIG. 5 shows a Raman spectrum for toluene (upper part), acetonitrile (centre) and cyclohexane (lower part) representing the optical signals.
Figure 5B:
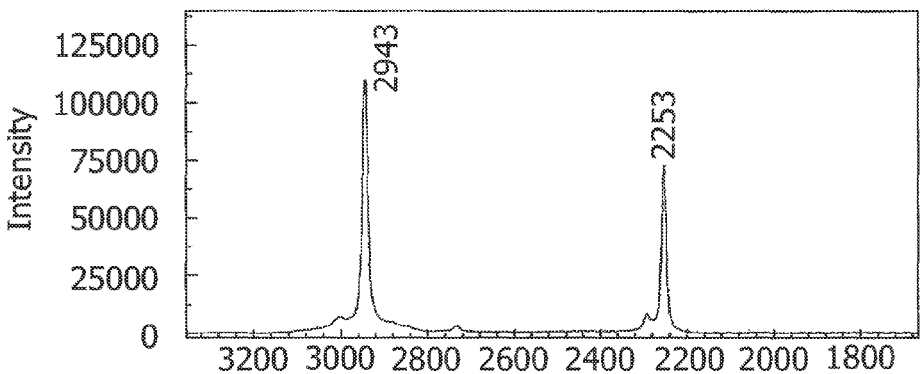
Figure 5C:
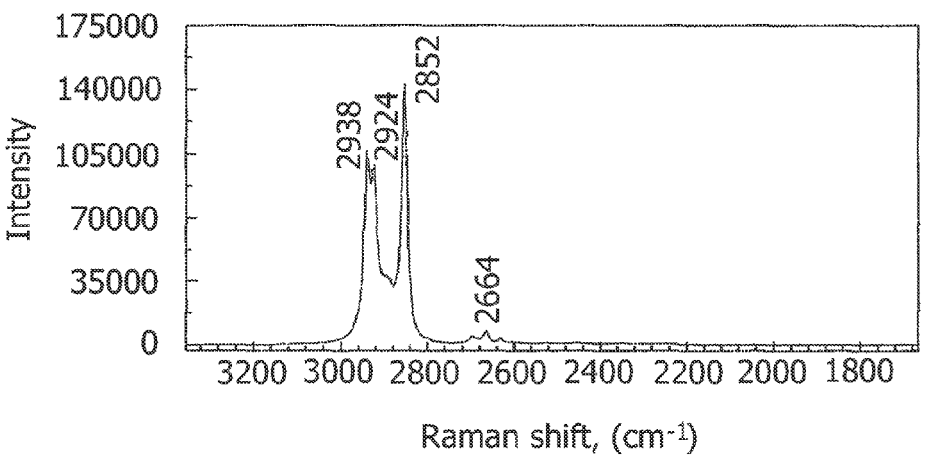
Figure 6:
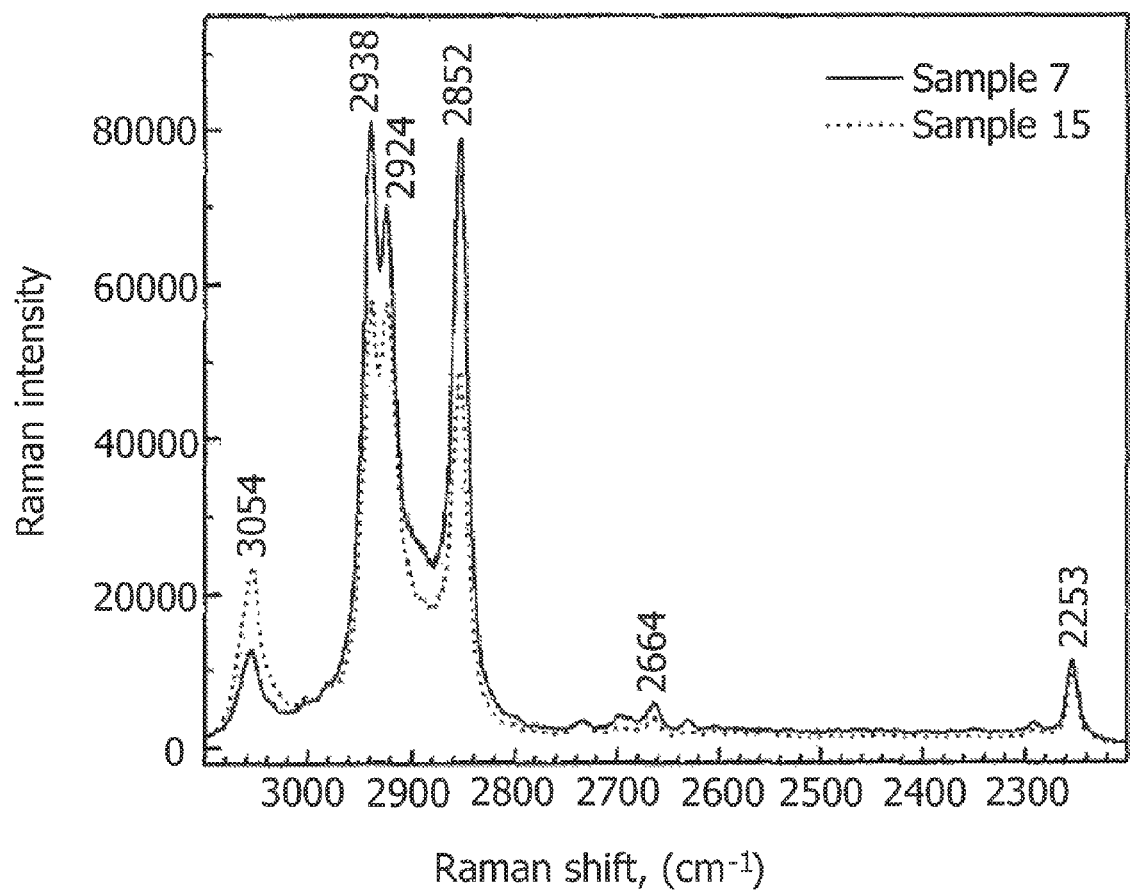
FIG. 6 shows the Raman spectra of two mixtures.

FIG. 5 shows the Raman spectra of mixtures 7 and 15.

The regression vectors for the three components of interest, namely toluene, acetonitrile and cyclohexane, were determined using a standard computational algorithms using the PLS Toolbox from Eigenvector Research, Inc., Manson, Wash., USA, which is based on the nonlinear iterative partial least squares (NIPALS) algorithm.

Figure 7A:
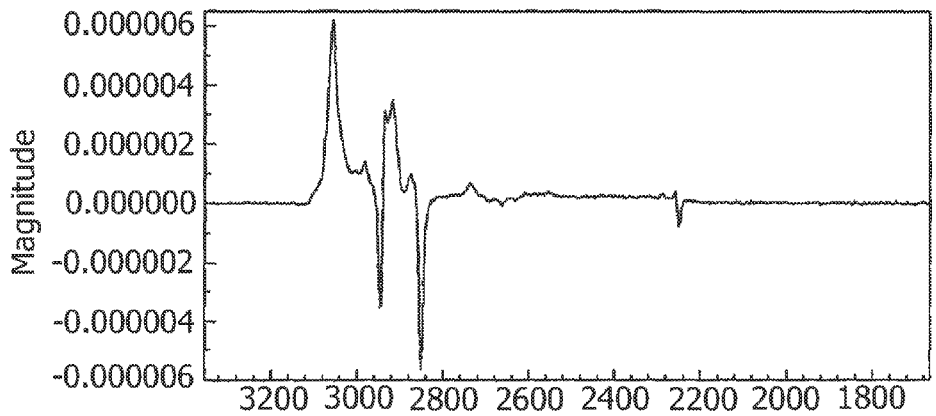
FIG. 7 shows the regression vectors for toluene (upper part), acetonitrile (centre) and cyclohexane (lower part) calculated for the three-components mixtures, i.e., mixtures, containing toluene, acetonitrile and cyclohexane.
Figure 7B:
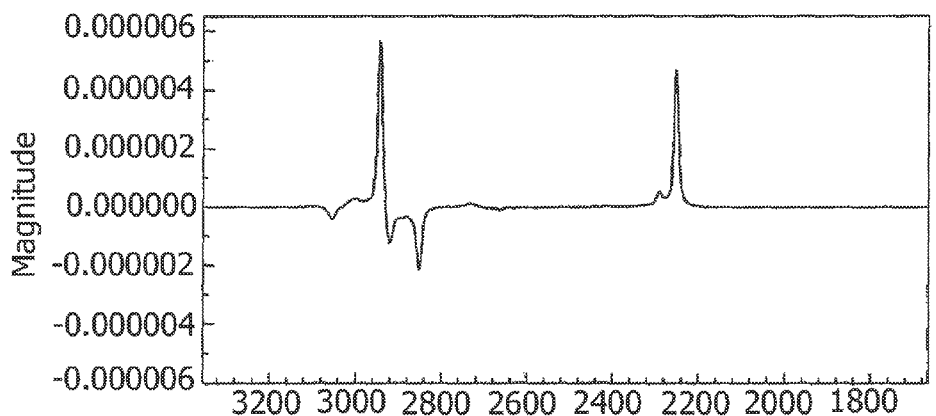
Figure 7C:
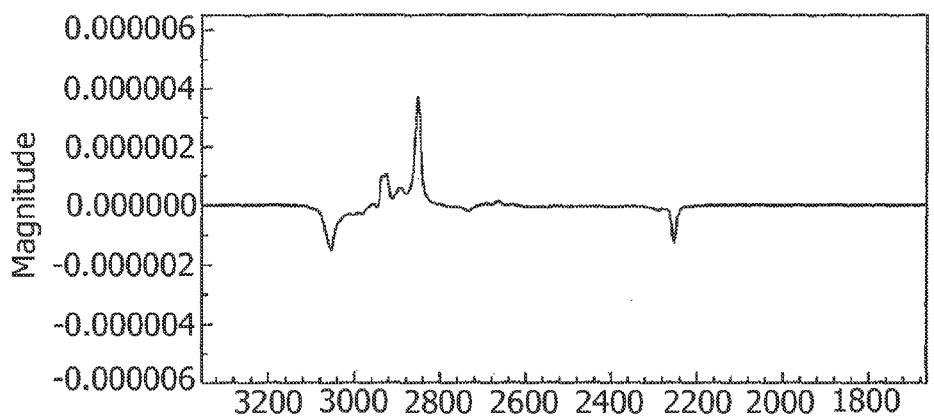

The pre-processing steps 1 to 4 mentioned above could be easily done in computer software. FIG. 7 shows the regression vectors of toluene (case a), acetonitrile (case b) and cyclohexane (case c). The y-axis is scaled equally for all three components. The regression vectors shown were obtained without pre-processing.

The prediction of the concentrations of the analytes of interest was done by "displaying" the regression vector for the analyte of interest on the LC cell and detecting the response weighed with the regression vectors. The prediction step was performed without using a multi-channel detector.

Figure 8:
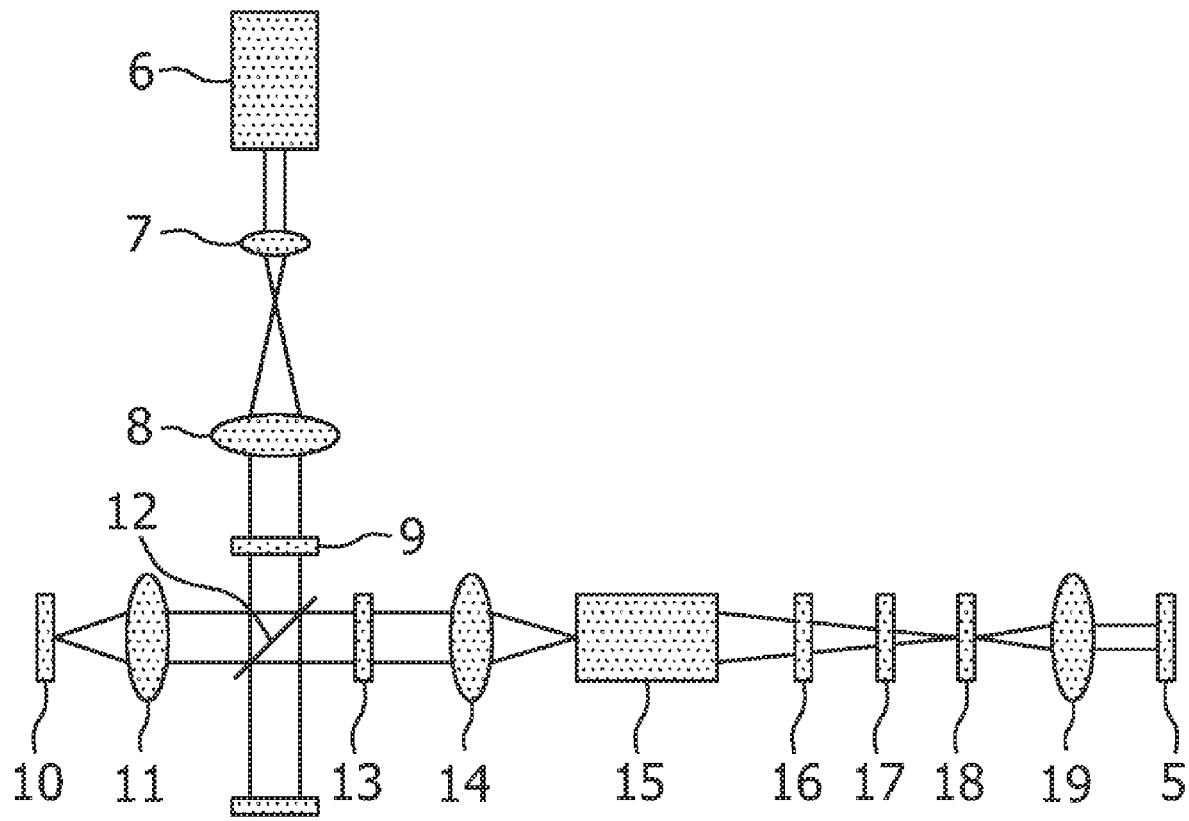
FIG. 8 shows the optical system for measurements during the prediction step, i.e. for determining the amount of an analyte contained in a mixture of analytes.

The setup is shown in FIG. 8. The pre-processing steps 1 to 4 mentioned above could be easily implemented in optical hardware as it was explained above.

A possible application of the method is blood analysis, including non-invasive blood analysis, to quantify concentrations of analytes in human blood such as glucose, cholesterol, lactate, triglycerides, albumin, urea, creatinine, haemoglobin or other analytes. One should understand that the method could also be applied to quantify analytes in tissue.

Further, the method can be used for analysing ingredients in food, for example for food quality control, for example to determine the fat content in milk.

Another possible application of the method could be found in plastic recycling industry, where plastic wastes have to be resorted in accordance to their types, or even more, where the same types of plastics have to be resorted in accordance to their grades or additives.

Another possible application of the method could be found in biomass conversion processes, where biomass is converted into fuels and valuable chemicals. For this application spectroscopic techniques and multivariate calibration could be applied to monitor chemical composition of a biomass feedstock.

Another possible application of the method could be found in quantifying the protein and moisture content of wheat and other grain products.

The method could be applied to optical spectra obtained by a variety of spectroscopic techniques, namely by Raman spectroscopy, coherent anti-Stokes Raman spectroscopy (CARS), surface-enhanced Raman spectroscopy (SERS), fluorescence, optical absorption spectroscopy in ultraviolet (UV), visible, near-infrared (NIR), and mid-infrared (MIR) region, etc.

FIG. 9 shows a block diagram of an embodiment of a spectroscopic device 29 of the invention.

The spectroscopic device 29 considered here is preferably mobile and/or portable. For example, the spectroscopic device 29 has a handle 30 such that it can be conveniently carried by a person. The spectroscopic device 29 has an optical processing component 31 for performing multivariate calibration in the optical domain. The optical processing component 31 comprises a VMOE, such as a VMOE device similar to the VMOE device 28 of FIG. 1.

Further, the spectroscopic device 29 has an electronic processing component 32, such as a microprocessor. The electronic processing component 32 is coupled to the optical processing component 31 for receiving the electrical signal that is generated by the optical processing component 31. For example, the electronic processing component 32 is coupled to an output of the photodiode of the VMOE device that delivers a signal in proportion to the inner product $RS^T$ (cf. photodiode 5 in the embodiment of FIG. 1).

The electronic processing component 32 serves for execution of program instructions 33 for processing the electrical signals provided by the optical processing component 31, such as for calculating the magnitude of a regression vector for an analyte contained in the sample 1.

Further, the electronic processing component 32 serves for execution of program instructions 34. The program instructions 34 are executed for evaluating a result of the quantitative chemical analysis provided by execution of the program instructions 33.

The electronic processing component 32 can be coupled to a storage component 35, such as a non-volatile storage component. At least one threshold value and/or condition or rule is stored in the storage component 35 for use by the program instructions 34 in order to perform the evaluation of the result of the quantitative chemical analysis.

For example, a threshold value for each of the analytes that are detected in the sample 1 is stored in the storage component 35. If the concentration of all considered analytes is below the respective threshold value the sample 1 is considered to be safe for consumption. On the contrary, if one or more of the threshold values is surpassed the result of the evaluation is that the food or beverage from which the sample 1 is taken is unsafe for consumption. Alternatively or in addition more complex conditions and/or rules, such as an expert system, can be implemented by the storage component 35 for performing more complex evaluations. Alternatively or in addition patient specific threshold values and/or conditions or rules are stored in the storage component 35 in order to take into account individual dietary requirements and/or medical conditions of the user of the spectroscopic device 29.

The spectroscopic device 29 has a user interface 36 for outputting a result of the evaluation performed by execution of the program instructions 34 and/or for outputting a result of the quantitative chemical analysis provided as a result of the signals outputted by the optical processing component 31 and of the following data processing operations performed by execution of program instructions 33.

The user interface 36 may have a display 37 and/or a printer 38 for outputting these results. In addition or alternatively the user interface 36 has control lamps 39, 40 and 41. For example, control lamp 39 can emit green light, control lamp 40 can emit yellow light and control lamp 41 can emit red light. If the control lamp 39 is switched on this indicates that the sample 1 is fit for consumption whereas if the control lamp 41 is switched on and red light is emitted this signals that the food or beverage from which the sample 1 is taken should not be consumed. If no clear judgment of the quality of the sample 1 is possible the yellow control lamp 40 is switched on in response to receiving respective control signals from the electronic processing component 32. The control lamps 39, 40 and 41 can be implemented using the discrete devices or by using the display 37, such as by displaying respective symbols on the display 37.

The spectroscopic device 39 may have a computer interface 42 for coupling to an external computer 43. The computer interface 42 can be implemented as a computer bus interface, such as a USB interface, as a blue tooth interface, or by another interface technology for wired or wireless communication with the computer 43. The result of the quantitative chemical analysis and/or of the evaluation provided by execution of the program instructions 33 and/or 34 can be communicated from the spectroscopic device 29 to the computer 43 via the computer interface 42 for storage, further evaluation and/or transmission such as to a server computer system or central database.

In one embodiment the electronic processing, i.e. execution of the program instructions 33 and/or 34, is at least partly performed by the computer 43. In particular, the spectroscopic device 29 might not have its own electronic processing component 32, storage 35 and/or user interface 36 but rely on respective components of the computer 43 instead. In this instance the spectroscopic device 29 may only be usable in conjunction with the computer 43. The later embodiment enables a particularly compact design of the spectroscopic device 29. It is to be noted that the computer 43 can be provided by any computational device, such as a laptop computer, personal digital assistance, mobile telephone or the like.

Embodiments of the invention can be used for detection of small amounts of methanol in an ethanol/water mixture, such as in alcoholic beverages, e.g. vodka. This is important for quality control of beverages, where methanol concentrations are varying within the range of 0.2-2% (v/v). If the concentration of the methanol is too high, this could lead to severe poisoning or death. The allowed values of the methanol concentration vary from country to country and depend on food standards provided by the respective regulatory authorities.

FIG. 10 shows the measured Raman spectra of 96% ethanol (solid line) and 99.8% methanol (dotted line). FIG. 11 shows the measured Raman spectrum of pure 99.8% methanol.

FIG. 12 shows the Raman difference spectrum of a mixture containing 47.2% ethanol and 1.6% methanol in water and 48% ethanol in water, respectively.

The positive Raman bands in the difference spectrum are due to methanol contribution, while the negative bands are due to decreased ethanol contribution. As can be seen from the FIG. 12, the small concentration of methanol in mixtures of ethanol and water is clearly detectable. Therefore, it is demonstrated that a VMOE-based spectroscopic device of the invention can be used for low-level methanol detection. It is to be noted that the accuracy of prediction of the methanol concentration can be improved by PLS calibration.

Further, it is to be noted that embodiments of the spectroscopic device of the invention can be implemented using a variety of spectroscopic modes and processes, including but not limited to florescence, phosphorescence, light scattering, UV, VIS, NIR and MIR absorption. For example, an embodiment of the spectroscopic device of the invention uses Raman spectroscopy at about 532 nm excitation and for emission wavelengths of in the order of 640 nm.

Further, it is to be noted that embodiments of the spectroscopic device of the invention can be used for analysis of component concentrations in a liquid, solid and/or gas phase of the sample 1.

LIST OF REFERENCE NUMERALS 01 sample/mixture
02 dispersive element
03 spatial light modulator (SLM)
04 lens
05 photo diode
06 laser
07 lens
08 achromatic doublet
09 half-lambda wave plate
10 absorption cell containing the sample
11 objective
12 dichroic beam splitter
13 holographic notch filter
14 lens (achromatic doublet)
15 spectrograph
16 retardation film
17 polarizer
18 LC panel
19 lens
20 lens
21 analyser
22 optical multi-channel analyser
23 power meter
24 motor
25 rotary table
26 signal generator
27 signal modification means
28 VMOE device
29 spectroscopic device
30 handle
31 optical processing component
32 electronic processing component
33 program instructions
34 program instructions
35 storage component
36 user interface
37 display
38 printer
39 control lamp
40 control lamp
41 control lamp
42 computer interface
43 computer program product
A axis

TABLE 1

| Sample number | Toluene | Acetonitrile | Cyclohexane |
|---|---|---|---|
| 1 | 1.00 | 0.00 | 0.00 |
| 2 | 0.00 | 1.00 | 0.00 |
| 3 | 0.00 | 0.00 | 1.00 |
| 4 | 0.50 | 0.50 | 0.00 |
| 5 | 0.50 | 0.00 | 0.50 |
| 6 | 0.06 | 0.47 | 0.47 |
| 7 | 0.25 | 0.25 | 0.50 |
| 8 | 0.25 | 0.50 | 0.25 |
| 9 | 0.50 | 0.26 | 0.24 |
| 10 | 0.21 | 0.50 | 0.29 |
| 11 | 0.31 | 0.20 | 0.50 |
| 12 | 0.50 | 0.30 | 0.20 |
| 13 | 0.20 | 0.30 | 0.50 |
| 14 | 0.30 | 0.50 | 0.20 |
| 15 | 0.49 | 0.20 | 0.30 |

The invention claimed is:

1. A spectroscopic device for quantitative chemical analysis comprising:
   a variable multivariate optical element configured to weigh an optical signal by a spectral weighing function, wherein the variable multivariate optical element performs multivariate calibration in the optical domain;
   an electronic processing component being adapted to evaluate the result of the quantitative chemical analysis; and
   a storage component for storing a threshold value and/or a condition and/or a rule, the electronic processing component being adapted to use the storage value and/or the condition and/or the rule for performing the evaluation of the result.

2. The spectroscopic device of claim 1 being portable.

3. The spectroscopic device of claim 2, comprising a handle for carrying the spectroscopic device by a person.

4. The spectroscopic device of claim 1 being operable for detection of at least one food component.

5. The spectroscopic device of claim 1 being operable for detection of at least one food decay product.

6. The spectroscopic device of claim 1 being operable for detection of at least one component of a liquid.

7. The spectroscopic device of claim 6, the liquid being water or a beverage.

8. The spectroscopic device of claim 6, the component being methanol.

9. The spectroscopic device of claim 1, the result of the evaluation being a quality information regarding a quality criterion of the food and/or liquid.

10. The spectroscopic device of 1, further comprising a user interface for outputting the result of the evaluation.

11. The spectroscopic device of claim 10, the user interface being adapted to display and/or print the result of the quantitative chemical analysis and/or the result of the evaluation.

12. The spectroscopic device of claim 10, the user interface comprising one or more control lamps for outputting the result of the evaluation.

13. The spectroscopic device of claim 1, further comprising a computer interface.

* * * * *